United States Patent
Myers Phipps et al.

(10) Patent No.: US 11,779,062 B2
(45) Date of Patent: *Oct. 10, 2023

(54) BREASTFEEDING GARMENT AND METHOD OF USE

(71) Applicant: LARKEN, LLC, Nichols Hills, OK (US)

(72) Inventors: Maggie Myers Phipps, Nichols Hills, OK (US); Kathleen Blouin, Arlington Heights, IL (US)

(73) Assignee: Larken, LLC, Nichols Hills, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/376,763

(22) Filed: Jul. 15, 2021

(65) Prior Publication Data

US 2021/0337886 A1 Nov. 4, 2021

Related U.S. Application Data

(63) Continuation of application No. 16/284,689, filed on Feb. 25, 2019, now Pat. No. 11,096,427.

(60) Provisional application No. 62/634,437, filed on Feb. 23, 2018.

(51) Int. Cl.
*A41C 3/04* (2006.01)
*A61M 1/06* (2006.01)

(52) U.S. Cl.
CPC ............... *A41C 3/04* (2013.01); *A61M 1/062* (2014.02); *A61M 1/064* (2014.02); *A61M 2209/088* (2013.01)

(58) Field of Classification Search
CPC .......................................... A41C 3/04
USPC ............................................. 450/36
See application file for complete search history.

(56) References Cited

U.S. PATENT DOCUMENTS

| | | |
|---|---|---|
| 2,425,145 A | 8/1947 | Coleman |
| 2,501,860 A | 3/1950 | Becker |
| 4,100,924 A | 7/1978 | Rosenberg |
| 4,909,771 A | 3/1990 | Bergman |
| 6,004,186 A | 12/1999 | Penny |
| 7,094,217 B2 | 8/2006 | Fialkoff |
| 9,155,339 B2 | 10/2015 | Alva |
| 2005/0028243 A1 | 2/2005 | Polzin |
| 2014/0220860 A1* | 8/2014 | Alva ................. A41C 3/04 450/36 |

* cited by examiner

*Primary Examiner* — Timothy K Trieu
(74) *Attorney, Agent, or Firm* — Barich IP Law Group

(57) ABSTRACT

A breastfeeding garment and method of use is provided. The breastfeeding garment includes a first front flap and a second front flap positioned over the breasts of a user, and a back panel, all of which are joined at two side seams. The first and second front flaps may be moved away from each other vertically to form an aperture through the breastfeeding garment. The first and second front flaps are composed of an elastic material, so a breastfeeding funnel may be placed onto the breast of a user through the aperture and then induced to remain in contact with the breast through the elastic force generated by the breastfeeding garment.

20 Claims, 2 Drawing Sheets

BREASTFEEDING GARMENT AND METHOD OF USE

CROSS-REFERENCE TO RELATED APPLICATIONS

The present application is a continuation of U.S. patent application Ser. No. 16/284,689, filed Feb. 25, 2019, entitled "Breastfeeding Garment and Method of Use," which claims the benefit of U.S. Provisional Application No. 62/634,437, filed Feb. 23, 2018, entitled "Breastfeeding Garment and Method of Use," all of which are hereby incorporated by reference in their entirety.

BACKGROUND OF THE INVENTION

Breastfeeding is recommended by the American Academy of Pediatrics, the World Health Organization and medical professionals worldwide as the preferred method for feeding infants. Unfortunately, there can be many challenges to implementing breastfeeding. Because of the increased awareness of the health benefits of breastfeeding for both infant and mother, and in light of the medical recommendations, many women are finding ways to provide their infants with breast milk even if the mothers are not physically present during the feeding or not physically able to directly breastfeed their infants. Some mothers have physical limitations which inhibit breastfeeding, such as inverted or sore nipples. In other cases, the infant has certain limitations, such as premature or low birth weight infants who have weak suckling abilities, infants with poor muscle tone, and "tongue tied", cleft lip or cleft palate infants who cannot create a seal between their mouth and the nipple. In addition to physical limitations, societal norms can create obstacles to breastfeeding and many women feel limited to breastfeeding in private.

The alternatives to full-time breastfeeding are either formula feeding, or feeding expressed human breast milk by bottle. Breast milk can be expressed, or released from the mother's lactating breasts, by massaging the breast by hand, or by the application of manual or electromechanical pumping equipment acting upon the breasts, both of which are commonly available in the domestic U.S. market. A traditional electric breast pump includes the funnel, a motor to generate the suction for the expression of milk, and a reservoir connected to the funnel to receive the expressed milk. Because of the duration and frequency required for breast milk expression, a woman may express both breasts simultaneously to increase efficiency. This process is often uncomfortable and time consuming. Further, without additional support, the funnel of a traditional breast pump often will not remain over the nipple on the breast; therefore, use of the pump requires the woman to hold it in place with her hands, thereby inhibiting her ability to simultaneously perform other activities. Hands-free pumping affords a mother the ability to perform other activities and/or simultaneously massage her breasts to enhance milk let down and minimize the potential for painful clogged ducts.

Efforts have been made to design brassieres that may be adjusted to give an infant access to a nursing woman's breast. For example, U.S. Pat. No. 2,501,860, issued Mar. 28, 1950, describes a brassiere with cups that allow an infant access to the woman's breasts. Access is provided by the woman detaching a flap of the brassiere at the top of each cup and folding back the fabric to reveal an opening in the fabric. The opening exposes the full breast and allows the infant to breastfeed from the mother.

Other conventional nursing garments may be configured for use with a breast pump. Many of these garments do not effectively hold the pump funnels in place, are uncomfortable and cumbersome for the wearer, or are impractical for daily wear. Often, the conventional garments include various attachments to secure a funnel of a breast pump to the wearer's breast. For example, zippers, elastic bands, slings, hooks, buttons, and the like may be used. Some conventional garments require additional devices or fabric pieces to be added or detached before the funnel can be secured. For example, U.S. Pat. No. 7,094,217, issued Aug. 22, 2006, describes the use of an elastic band to secure a funnel of a pump and the use of a latch to secure portions of the brassiere when the wearer is not expressing milk.

Existing garments designed to support hands free pumping are also largely configured to be worn only during periods when milk is being expressed, thereby, requiring a garment change before and after expressing milk, which increases the burden on the woman expressing milk. For example, U.S. Pat. No. 6,004,186, issued Dec. 21, 1999, describes a garment (e.g., a halter top, a bandeau, a tube top) that the woman wears to secure a funnel of a breast pump to her breast. Breast pump funnels may be inserted into two openings in a central area of each side of the garment. Accordingly, there continues to be a need for garments that both assist a woman in expressing milk and provide the support, style, discretion, and/or comfort desired by the woman during periods between milk expressing sessions.

BRIEF SUMMARY OF THE INVENTION

One or more of the embodiments of the present invention provide a breastfeeding garment having a back panel, a first front flap and a second front flap, which are joined at two side seams. The breastfeeding garment is positioned over the breasts of a user and the first and second front flaps may be moved away from each other vertically to form an aperture through the breastfeeding garment. The first and second front flaps are composed of an elastic material, so a breastfeeding funnel may be placed onto the breast of a user through the aperture and then induced to remain in contact with the breast through the elastic force generated by the breastfeeding garment.

DETAILED DESCRIPTION OF THE INVENTION

Figure 1:
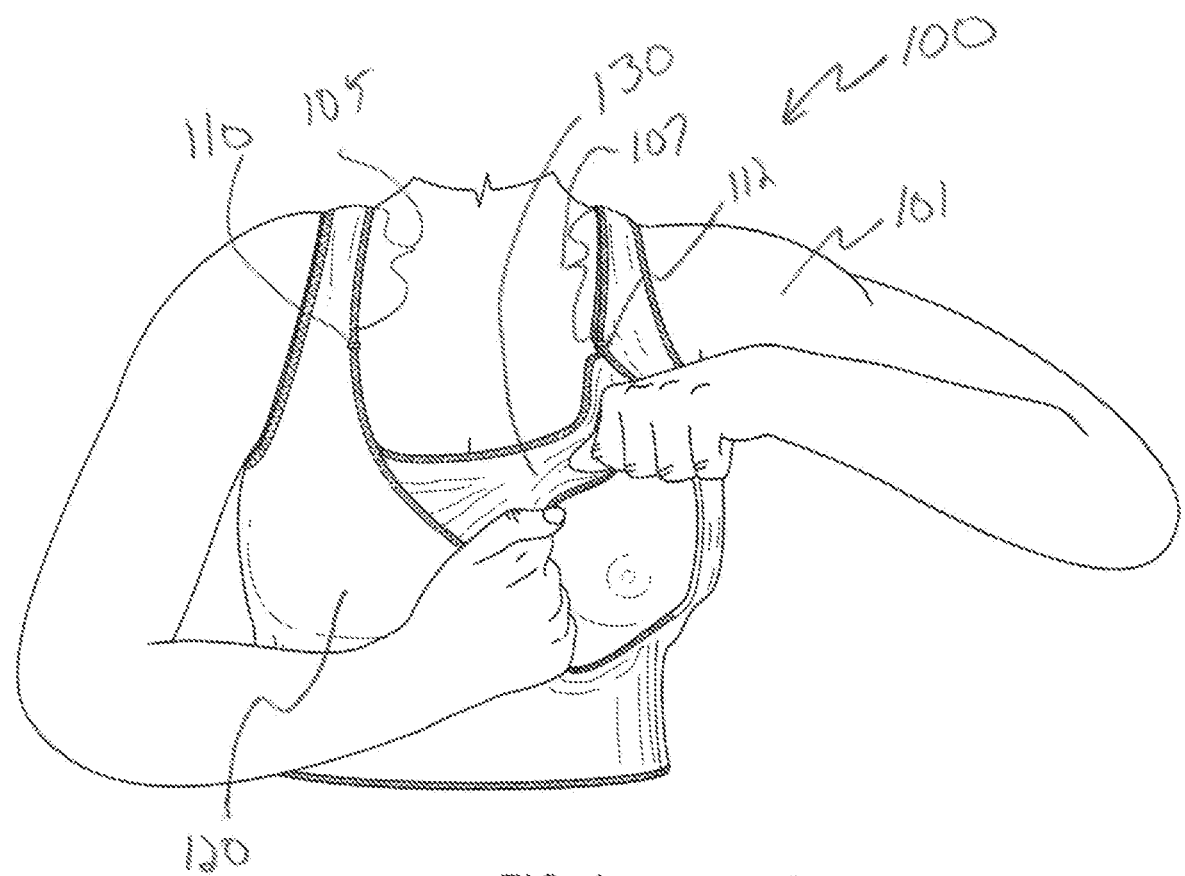
FIG. 1 illustrates a breastfeeding garment according to an embodiment of the present invention.

One or more embodiments of the subject garment may not only hold the funnels in place securely so that the mother does not require the use of her hands to do so, but it also can also be worn all day with or without a nursing bra of the mother's choice, which enables the wearer to access the breasts and pump hands free without needing to undress and redress each instance, thereby saving a significant amount of time for the mother and maximizing comfort. The stretch and recovery of the fabric and construction of the garment accommodate and support the natural expansion and contraction of the woman's breasts, and the garment may be constructed in one or more embodiments without snaps, zippers, hooks, elastic or other cumbersome hardware that may be difficult to manipulate, uncomfortable for the wearer, and potentially irritating to the baby's skin and/or mother's skin. The absence of any hardware also provides the mother with easy access to the breasts during hands free pumping so that she may massage the breasts to enhance milk let down and minimize the potential for formation of painful and clogged ducts.

Product Description

One or more embodiments of the garment of the present disclosure may enable engagement of one or more funnels of one or more breast pumps without slings, hooks, snaps, buttons, hook-and-loop attachments, latches, or the like to secure a funnel to a breast. Separate devices or material pieces do not need to be added or detached to enable access to the breast by either the funnel or an infant. One or more embodiments of garments of the present disclosure may enable engagement with and disengagement of the funnel without disrobing and while the woman is wearing the garment, which may reduce the risk of spilling expressed milk; the garments of the present disclosure may also be worn as a functional undergarment or layering piece for an extended length of time. One or more embodiments of the present disclosure do not define permanent holes or openings at the center of each side of the garment and cover the breasts while accommodating the natural expansion and contraction of a nursing woman's breasts. The garments may also enable direct breastfeeding of an infant, in addition to enabling hands-free pumping. One or more embodiments of the present disclosure includes an outer and an inner material layer that both fully cover the breast and nipple without openings in the layers at the nipple. Moreover, one or more embodiments of the present disclosure may include free edges that may be manipulated to define an opening for the funnel and enable positioning of the funnel anywhere on the breast.

Accordingly, disclosed is a garment for a nursing woman that allows the woman to both nurse a child discreetly and pump breastmilk hands free. The garment is comprised of a lightweight breathable moisture wicking fabric with excellent stretch and recovery to adjust to a woman's changing post-partum body. In one embodiment, the fabric may weigh 155 grams per square meter (gsm). In other embodiments it may weigh as low as 100 grams per square meter and up to as high as 275 grams per square meter. It is made with a material of sufficient elasticity and strength that when worn in the "x" method described below, it firmly and frictionally holds the funnel portion of a breast pump against each breast during the complete breast milk expression operation.

It can be worn with or without a bra, including all nursing bras, and is compatible with most breast pumps. For example, a user may position a standard nursing-type bra over their breasts. The nursing-type bra may include a flap that is openable to expose the nipple of the breast for feeding, but wherein said flap also engages with said bra to cover said nipple when feeding is not desired. After the nursing-type bra is positioned, one or more embodiments of the present garment may be positioned over said bra in the standard configuration discussed herein. When feeding is desired, the front flaps of the garment may first be positioned to establish an opening as described herein and the flap of the nursing-type bra may then be disengaged from the bra to provide access to the nipple for feeding.

In one embodiment, the garment is a single layer across the back forming a back panel and two layers in the front, which are sewn together along the side seams, through the arm holes and through a portion of the neckline straps extending from the shoulder down to a bar tack or horizontal stitch. In one embodiment, the bar tack or horizontal stitch is located between 0.5 and 6 inches below the shoulder on both the right and left sides of the neckline. There are free edges on the bottom seam running below the breasts and free edges partially through the neckline between the bar tacks or horizontal stitches on each side.

To nurse, a wearer may simply pull both layers of the garment above the breast from the hem, or the wearer may pull both layers of the garment below the breast from the neckline. To pump hands free, the user repositions the two front layers into an X design by pulling up the outer most layer over nipple on one side for a first breast and pulling the inner most layer down from the neckline and below the nipple on that same side to provide access to the first breast. The opposite is done on the other side for the second breast. The inner most layer is pulled above the nipple and the outer most layer is pulled below the nipple to provide access to the second breast. Alternatively, the user could first pull down the outer most layer over nipple on one side for a first breast and pull the inner most layer up and above the nipple on that same side to provide access to the first breast. The user would then do the opposite on the other side for the second breast. In that scenario, the inner most layer would be pulled below the nipple and the outer most layer is pulled above the nipple to provide access to the second breast. Once the layers are positioned to provide access to a breast, nursing may be performed directly. Alternatively, a funnel of a breast pump may be positioned between and engage with the bottom edge of the outer most layer and the top edge of the inner most layer by one or more of friction between the layers and the breast skin, elastic or spring force of the layers pressing the funnel against the skin of the breast, and/or vertical force between the bottom edge of the outer most layer and the top edge of the inner most layer. A funnel of a breast pump could also be positioned between and engage with the bottom edge of the inner most layer and the top edge of the outer most layer by one or more of friction between the layers and the breast skin, elastic or spring force of the layers pressing the funnel against the skin of the breast, and/or vertical force between the bottom edge of the inner most layer and the top edge of the outer most layer.

In one embodiment of the design, users also have the option to nurse on one side while simultaneously pumping on the other side. To do so, the wearer would simply pull both layers up over the breast that is being used to nurse or pull both layers down under that breast. The wearer would then pump on the opposite breast by pulling one layer above the funnel of the pump and one layer below the funnel of the pump.

The wearer may also use the garment to keep the upper portion of the breast and the wearer's chest covered for discreet infant feeding. It can be worn under a separate garment that provides easy access to the breast, such as one that can be pulled down at the neckline or a button down top. The wearer would then simply pull the subject garment above the breast being used to nurse to maintain coverage above and around the breast.

In one embodiment, to provide desirable stretch and recovery and/or to provide a lightweight breathable, moisture-wicking fabric, the fabric may be a polyester spandex blend with up to 30% spandex or lycra and as low as 3% spandex or lycra. In another embodiment, the fabric is a micromodal spandex blend with up to 30% spandex or lycra and as low as 3% spandex or lycra. In another embodiment, the fabric is a nylon spandex blend with up to 30% spandex or lycra and as low as 3% spandex or lycra. In another embodiment, the fabric is a rayon spandex blend with up to 30% spandex or lycra and as low as 3% spandex or lycra. The fabric may be stretched to at least 50% more of its resting state.

As mentioned above, the fabric is held securely against the wearer's body and when the X design is made, so that the garment supports the pump parts and bottles as they fill with breastmilk. In one embodiment, the garment is made using one or more of the fabric examples above so that the garment may support up to 6 ounces of breastmilk on each breast, for a total of 12 ounces at a single time. In another embodiment, the garment will support between zero and 5 ounces of breastmilk on each side.

As noted above, the two front layers may be sewn together partially through the neckline from the shoulder down to a bar tack or horizontal stitch located on the inner seam of each of the straps. This provides additional support for the funnels and connecting breast milk bottles to ensure that the user can pump hands free, a secure suction to the breast is maintained to maximize breastmilk output, and the bottles will stay in place during pumping without spilling. The bar tacks or horizontal stitches ensure that the seams stay securely sewn together as the garment is stretched in various directions.

In one embodiment, the layers are sewn together at the side seam through a flatlock seam, which minimizes chafing and allows the wearer to move comfortably with ultimate stretch and recovery at the sides. In another embodiment, a serged seam is used at the side seam. Having the layers sewn together at the side seam maximizes the resistance of the garment against the wearer's body as the layers are pulled in opposite directions to pump to again best support the pump parts and maintain a secure suction of the funnel against the wearer's breast.

The stitch used throughout the neckline is a very high stitches per inch ("spi") coverstitch to ensure that the neckline can be stretched several times below and above the breast and pump parts while maintaining its shape to again provide excellent stretch and recovery. In one embodiment, during construction, the fabric for the neckline is cut on the bias to also ensure that each layer can be pulled completely above the breast from the hem and can be pulled to the base of the breast from the neckline.

In one embodiment, a nylon thread having a weight of between 18 to 36 grams per 1000 meters of yarn and an average breaking strength of at least 1 pound of force is used throughout the stitches in the garment. In another embodiment, a polyester thread having a weight between 18 to 36 grams per 1000 meters of yarn and an average breaking strength of at least 1 pound of force is used throughout the stitches in the garment. The weight and strength of the thread enables the neckline to be pulled in all directions without the stitches breaking and while maintaining the garment's shape.

Unlike other garments on the market that can be used to pump hands free, the subject garment provides hands free support without the use of any cumbersome hardware, such as zippers, snaps, and elastic, which is irritating to a baby and mother's sensitive skin, difficult for a mother to undo and adjust to nurse, and can cause clogged ducts when breastfeeding.

FIG. 1 illustrates a breastfeeding garment 100 according to an embodiment of the present invention. As shown in FIG. 1, the breastfeeding garment 100 is positioned on the torso of a user 101. The breastfeeding garment 100 includes a first neckline strap 105, a second neckline strap 107, a first bar tack or horizontal stitch 110, a second bar tack or horizontal stitch 112, a first front flap 120, and a second front flap 130. As shown in FIG. 1, the first front flap 120 may be pulled downward by the user 101 while the second front flap 130 is pulled upward in order to expose the breast.

Figure 2:
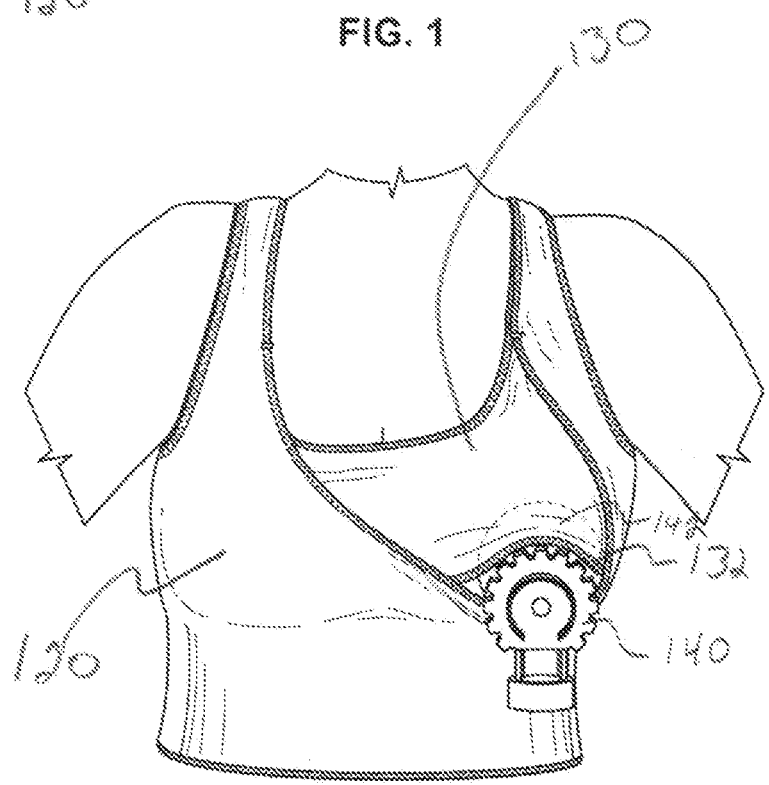
FIG. 2 illustrates the breastfeeding garment of FIG. 1 with a first breast pump funnel positioned on the breast.

Next, as shown in FIG. 2, a first breast pump 140 having a first breast pump funnel 142 may be positioned on the breast. The bottom edge 132 of the second front flap 130 is positioned outside the first breast pump funnel 142 in order to induce the first breast pump funnel 142 into contact with the breast. Additionally, top edge 122 of the first front flap 120 is positioned outside the first breast pump funnel 142 in order to induce the first breast pump funnel 142 into contact with the breast. Consequently, the first breast pump 140 is maintained in contact with the breast by the spring force or elastic force of the front flaps 120, 130.

Figure 3:
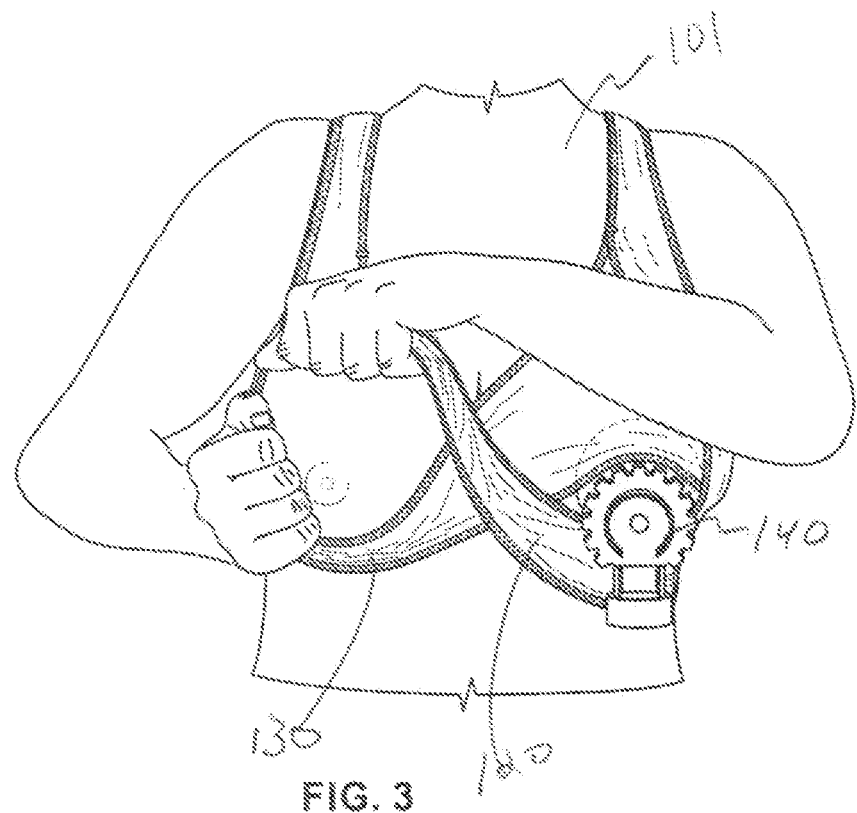
FIG. 3 illustrates the breastfeeding garment of FIG. 1 with a first front flap pulled upward by the user while the second front flap is pulled downward in order to expose the other breast.

Similarly, as shown in FIG. 3, in the region of the other breast, the first front flap 120 may be pulled upward by the user 101 while the second front flap 130 is pulled downward in order to expose the other breast. The first breast pump 140 remains undisturbed.

Figure 4:
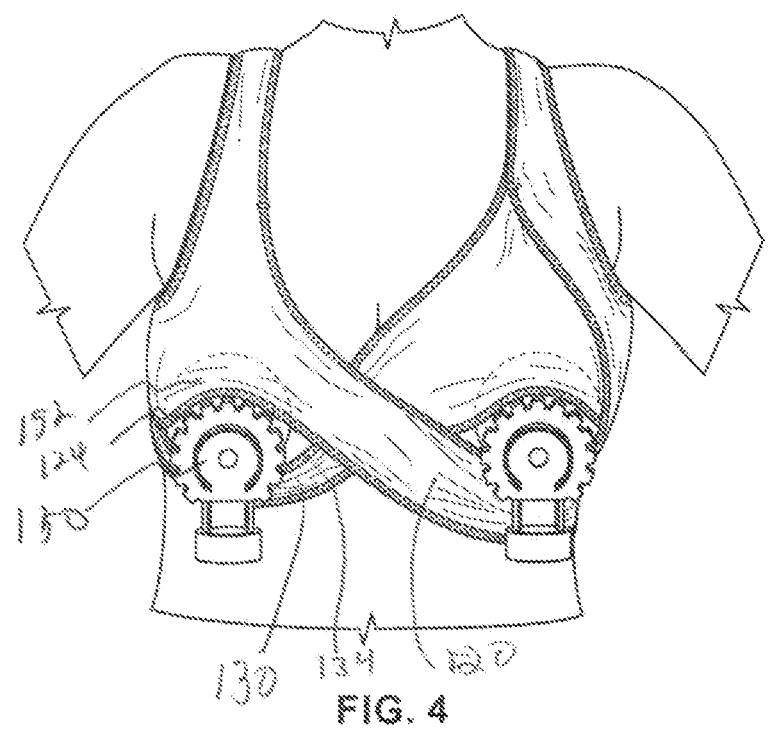
FIG. 4 illustrates the breastfeeding garment of FIG. 3 with a second breast pump funnel positioned on the other breast.

As shown in FIG. 4, a second breast pump 150 having a second breast pump funnel 152 may be positioned on the other breast. The bottom edge 124 of the first front flap 120 is positioned outside the second breast pump funnel 152 in order to induce the second breast pump funnel 152 into contact with the breast. Additionally, the top edge 134 of the second front flap 130 is positioned outside the second breast pump funnel 152 in order to induce the second breast pump funnel 152 into contact with the breast. Consequently, the second breast pump 150 is maintained in contact with the breast by the spring force or elastic force of the front flaps 120, 130.

Although FIGS. 1-4 illustrate the breastfeeding garment 100 in a configuration supporting a first breast pump 140 and a second breast pump 150 where the first breast pump is positioned in the breastfeeding garment first, in an alternative embodiment, the second breast pump 150 may be positioned in the breastfeeding garment first. In additionally alternative embodiments, the breastfeeding garment may be employed with only one of the first breast pump 140 and second breast pump 150 installed.

Additionally in an alternative embodiment, the "X" shape created by the positioning of the front flaps 120, 130 may also be positioned opposite of how it is shown in the Figures. In this embodiment, instead of the first front flap 120 pulling down and the second front flap 130 pulling up over the exposed breast in FIG. 1, the garment may be positioned with the second front flap 130 pulled down over the breast exposed in FIG. 1 and the first front flap 120 pulled up over the exposed breast in FIG. 1, which provides the opposite configuration to that shown in the Figures. Similarly, the configuration for the other breast may also be inverted from that shown.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A breastfeeding garment including:
   a left front flap, wherein said left front flap is configured to be positioned over both breasts of a user in a first configuration, said left front flap including:
      a top left front flap connection with a left neckline strap;
      a left side left front flap connection along a left side seam;
      a right side left front flap connection along a right side seam;
      a left front flap bottom edge; and
      a left front flap top edge;
   a right front flap, said wherein said right front flap is configured to be positioned over both breasts of said user in the first configuration, said right front flap including:
      a top right front flap connection with a right neckline strap;
      a right side right front flap connection along said right side seam;
      a left side right front flap connection along said left side seam;
      a right front flap bottom edge; and
      a right front flap top edge; and
   a back panel, wherein said back panel, said left front flap and said right front flap are joined along said left side seam and said right side seam,
   wherein said left front flap and said right front flap are formed of elastic material,
   wherein said left front flap is configured to be induced away from said right front flap to form an aperture through said breastfeeding garment between one of said left front flap bottom edge and said right front flap top edge and said left front flap top edge and said right front flap bottom edge to allow a breast pump funnel to be placed on a breast through said aperture.

2. The breastfeeding garment of claim 1 wherein at least one of said top left front flap connection and said top right front flap connection is a bar tack.

3. The breastfeeding garment of claim 1 wherein at least one of said top left front flap connection and said top right front flap connection is a horizontal stitch.

4. The breastfeeding garment of claim 1 wherein said left front flap is configured to be induced away from said right front flap to form a second aperture through said breastfeeding garment to allow a second breast pump funnel to be placed on a second breast through said second aperture.

5. The breastfeeding garment of claim 1 wherein at least one of said left front flap and said right front flap is composed of a polyester spandex blend.

6. The breastfeeding garment of claim 1 wherein at least one of said left front flap and said right front flap is composed of a polyester blend.

7. The breastfeeding garment of claim 1 wherein at least one of said left front flap and said right front flap is composed of a micromodal spandex blend.

8. The breastfeeding garment of claim 1 wherein at least one of said left front flap and said right front flap is composed of a nylon blend.

9. The breastfeeding garment of claim 1 wherein at least one of said left front flap and said right front flap is composed of a lycra blend.

10. The breastfeeding garment of claim 1 wherein at least one of said left front flap and said right front flap is composed of a rayon blend.

11. A method of positioning a breast pump funnel, said method including:
    positioning a breastfeeding garment on a user, wherein said breastfeeding garment includes:
       a left front flap composed of an elastic fabric, wherein said left front flap is positioned over both breasts of a user in a first configuration, said left front flap including:
          a top left front flap connection with a left neckline strap;
          a left side left front flap connection along a left side seam;
          a right side left front flap connection along a right side seam;
          a left front flap bottom edge; and
          a left front flap top edge;
       a right front flap composed of an elastic fabric, wherein said right front flap is positioned over both breasts of said user in the first configuration, said right front flap including:
          a top right front flap connection with a right neckline strap;
          a right side right front flap connection along said right side seam;
          a left side right front flap connection along said left side seam;
          a right front flap bottom edge; and
          a right front flap top edge; and
       a back panel, wherein said back panel, said left front flap and said right front flap are joined along said left side seam and said right side seam;
    inducing said left front flap away from said right front flap to form an aperture between one of said left front flap bottom edge and said right front flap top edge and said left front flap top edge and said right front flap bottom edge through said breastfeeding garment; and
    positioning a breast pump funnel on a breast of said user through said aperture.

12. The method of claim 11 wherein at least one of said top left front flap connection and said top right front flap connection is a bar tack.

13. The method of claim 11 wherein at least one of said top left front flap connection and said top right front flap connection is a horizontal stitch.

14. The method of claim 11 further including inducing said left front flap away from said right front flap at a second location to form a second aperture through said breastfeeding garment; and
    positioning a second breast pump funnel on a second breast of said user through said second aperture.

15. The method of claim 11 wherein at least one of said left front flap and said right front flap is composed of a polyester spandex blend.

16. The method of claim 11 wherein at least one of said left front flap and said right front flap is composed of a polyester blend.

17. The method of claim 11 wherein at least one of said left front flap and said right front flap is composed of a micromodal spandex blend.

18. The method of claim 11 wherein at least one of said left front flap and said right front flap is composed of a nylon blend.

19. The method of claim 11 wherein at least one of said left front flap and said right front flap is composed of a lycra blend.

20. The method of claim 11 wherein at least one of said left front flap and said right front flap is composed of a rayon blend.

* * * * *